June 13, 1950 H. C. SWIM Plant Pat. 952
ROSE PLANT
Filed April 26, 1949
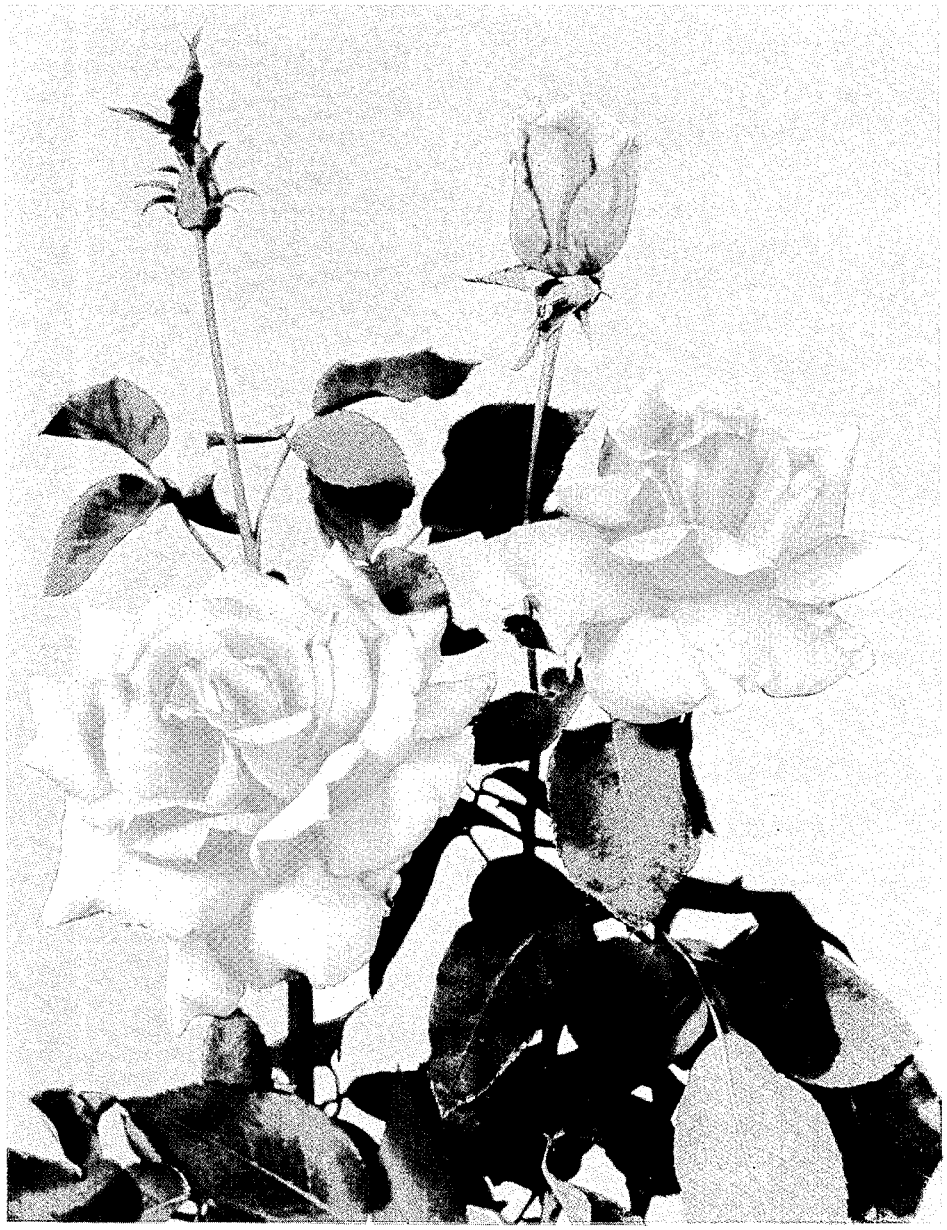
Inventor
H. C. Swim
By Robb & Robb
Attorneys Patented June 13, 1950

Plant Pat. 952

UNITED STATES PATENT OFFICE

952

ROSE PLANT

Herbert C. Swim, Ontario, Calif., assignor to Armstrong Nurseries, Inc., Ontario, Calif., a corporation of California Application April 26, 1949, Serial No. 89,779

1 Claim. (Cl. 47—61)

This invention relates to a new and distinct variety of rose plant, originated by crossing the bush variety "Christopher Stone" and well-known variety "Charlotte Armstrong."

The distinctive or dominating characteristics of this new variety comprise the following:

(1) A vigorous habit of growth combined with a trait of usually producing a single flower to a stem.

(2) The combination of the graceful form of the bud, the well-balanced open bloom, the strong and sweet fragrance of the bloom, and the manner in which these blooms are produced on long individual stems. These qualities make the variety near ideal for cutting and bouquets and for exhibition.

(3) The color of the flower combined with the long bud and the well balanced open flower with this particular type of fragrance, which is mixed tea and spicy.

(4) The relatively large foliage, with greater than average resistance to mildew, the size of which was obtained by using "Christopher Stone" as the seed parent and the mildew resistance of which was obtained by using "Charlotte Armstrong" as the pollen parent.

This new variety is distinct from its seed parent in the following way:

(1) A much more vigorous habit of growth of the plant.

(2) This new variety has flowers that would popularly be described as pink whereas the flowers of "Christopher Stone" are popularly described as red or scarlet crimson.

(3) This new variety produces its flowers predominantly singly, whereas "Christopher Stone" produces a much larger proportion of its flowers in clusters.

(4) The flowers of this new variety are strongly fragrant, whereas the flowers of "Christopher Stone" are only mildly fragrant.

This new variety is distinct from its pollen parent as follows:

(1) This new variety has larger foliage than its seed parent.

(2) The canes are longer and of heavier caliper than those of "Charlotte Armstrong" and are characterized by having very few small prickles, whereas the canes of "Charlotte Armstrong" are characterized by having many small prickles.

(3) This new variety has no prickles on the under side of the rachis, whereas "Charlotte Armstrong" does have prickles on the under side of the rachis.

(4) This new variety has a flower that is popularly described as pink, whereas the flowers of "Charlotte Armstrong" are described as varying from red through flame, to cerise.

(5) This new variety has a strongly fragrant flower, whereas the fragrance of the flowers of "Charlotte Armstrong" is mild or slight.

This new variety was asexually reproduced at Ontario, California, by budding.

In the accompanying drawing specimens of the foliage and flowers at different stages of development are shown.

The following is a detailed description of the new variety, all references to color being in accordance with the Robert F. Wilson Horticultural Colour Chart, 1938, except where indicated to be in accordance with Ridgway's Color Standards and Nomenclature:

Type: Tall; bush; outdoor; seedling.
Class: Hybrid tea.
Breeding: Seedling.
*Seed parent.*—"Christopher Stone" (unpatented).
*Pollen parent.*—"Charlotte Armstrong" (Pl. Pat. No. 455).
Propagation: Holds its distinguishing characteristics through succeeding propagations by budding.

*Flower*

Locality where grown: Ontario, California.
Flowers borne: Usually singly, sometimes two or more to stem; on strong, medium to long stems.
Quantity of bloom: Free; outdoors.
Continuity: Nearly continuous during growing season.
Fragrance: Moderate to strong; tea; spicy.
Bud:
*Peduncle.*—Average length to long; average caliper; erect; smooth except for some gland-tipped cilia. Color—Biscay Green, Plate XVII (Ridgway), washed in upper portions with Vandyke Red, Plate XIII (Ridgway).
*Before calyx breaks.* — Size — medium. Form—medium length; pointed; with foliaceous appendages and with slender foliaceous parts extending beyond the tip of the bud equal to one-fourth or more of its length.
*As calyx breaks.*—Color—Chrysanthemum Crimson, Plate 824/1, page 169, with shadings of Oxblood Red, Plate 00823, page 191, where most exposed to the sun.

3

Bud—Continued

*Sepals.*—Inner surface with woolly tomentum; margins covered have tomentum, exposed margins have gland-tipped cilia. Color of sepals from a newly open flower—inside—near Pistachio Green, Plate XLI (Ridgway); outside—Turtle Green, Plate XXXII (Ridgway).

*As first petal opens.*—Size—average to large. Form—long; pointed to slightly urn-shaped. Color—outside—Rose Red, Plate 724/2, page 158; inside—Rose Red, Plate 724/1, page 158.

*Opening.*—Opens up well. Is not retarded from opening by cold or dry weather.

Bloom:

*Size, when fully open.*—Large; 3¼″ to 4½″.

*Petalage.*—Double; from 30 to 37 petals, plus 6 to 9 petaloids; arranged regularly.

*Form.*—High centered at first; becoming flat to cupped; petals at first loosely rolled outward; becoming later at maturity somewhat flat with margins of outer petals loosely rolled outward.

Petals:

*Texture.*—Medium thick; with inside velvety and outside slightly satiny.

*Shape.*—Outside—broadly obovate with apex rounded. Intermediate—obovate with apex sub-acute. Inside—obovate approaching cuneate with apex rounded.

*Color.*—Colors may be modified by fading or by being overlaid with other colors.

This description of a newly opened flower was made from a rose grown outdoors in the month of October, at Ontario, California:

*Color.—Outside petal*—outside surface: between Tyrian Rose, Plate 24/1, page 24, and Tyrian Rose, Plate 24, page 24; inside surface: Tyrian Rose, Plate 24/1, page 24. *Intermediate petal*— outside surface: between Crimson, Plate 22/1, page 22, and Crimson, Plate 22, page 22; inside surface: Rose Red, Plate 724/1, page 158. *Inner petal*— outside surface: between Crimson, Plate 22/1, page 22, and Crimson, Plate 22, page 22; inside surface: Rose Red, Plate 724/1, page 158.

This description was made from a rose that was open for three days outdoors in the month of October, at Ontario, California::

*Color.—Outside petal*—outside surface: between Tyrian Rose, Plate 24/2, page 24, and Tyrian Rose, Plate 24/1, page 24; inside surface: between Tyrian Rose, Plate 24/2, page 24, and Tyrian Rose, Plate 24/1, page 24. *Inside petal*—outside surface: near Tyrian Rose, Plate 24/2, page 24; inside surface: between Tyrian Rose, Plate 24/2, page 24, and Tyrian Rose, Plate 24/1, page 24.

*General color effect.*—Newly opened flower—Rose Red, Plate 724/1, page 158. Three days open—Tyrian Rose, Plate 24/2, page 24.

*Behavior.*—Drop off cleanly except for occasional petaloids; fading to Rhodamine Pink, Plate 527, page 138, over most of petal with edges fading to Rhodamine Pink, Plate 527/3, page 138.

*Flower longevity.*—On bush in garden—4 days in October. Cut roses grown outdoors kept at living-room temperatures—3 days in October.

4

*Reproductive organs*

Stamens: Average number; arranged regularly about pistils, a few mixed with petaloids.

Filaments: Medium length; most with anthers. Color—Begonia, Plate 619, page 146 (12 mm. long).

Anthers: Medium size; all open at once approximately. Color—central portions—Aureolin, Plate 3/2, page 3; outer portions—Buttercup Yellow, Plate 5/2, page 5.

Pollen: Moderate quantity. Color—Buttercup Yellow, Plate 5/2, page 5.

Pistils: Many, approximately 100 in number.

Styles: Moderately even; average length; average caliper; bunched. Color—Claret Rose, Plate 021, page 109.

Stigma: Saffron Yellow, Plate 7/3, page 7, with translucent effect.

Ovaries: Most enclosed in calyx.

Hips: Average to large size; turbinate; moderately smooth; walls thick, fleshy. Color—Clear Dull Green-Yellow, Plate XVII (Ridgway), overlaid with Light Coral Red, Plate XIII (Ridgway).

Sepals: From mature hips—permanent; medium length to long; reflexed. Color—inside: Deep Chrysolite Green, Plate XXXI (Ridgway), fading toward the margins to Lime Green, Plate XXXI (Ridgway); outside: Light Grape Green, Plate XLI (Ridgway) fading to Chrysolite Green, Plate XXXI (Ridgway), toward the margins.

Seed: Average number; usually medium size; 14 to 22 in number.

*Plant*

Foliage:

*Leaves.*—Compound of usually 3 to 5 leaflets; normal quantity; large; somewhat leathery.

*Leaflets.*—Shape—ovate with apex narrowly acute; base round; margin doubly serrate.

*Color.—Mature*—upper surface: Parsley Green, Plate 60962, page 193; under surface: Mytho Green, Plate XLI (Ridgway) overlaid on Peacock Green, Plate VI (Ridgway). *Young*—upper surface; Scheele's Green, Plate 860/2, page 175, overlaid with Vandyke Red, Plate XIII (Ridgway); under surface: Mineral Red, Plate XXVII (Ridgway).

*Rachis.*—Average size. Upper side—grooved with some stipitate glands on edges; under side—smooth.

*Stipules.*—Medium length; medium width, with medium length points, turning out at an angle of more than 45°, recurved toward the rachis.

*Disease.*—More than average resistant to mildew.

Growth:

*Habit.*—Bushy; upright; moderately branched.

*Growth.*—Vigorous.

*Canes.*—Medium caliper to heavy.

*Main stems.*—Color—Deep Dull Yellow-Green, (1) Plate XXXII, (Ridgway). *Large prickles*—several; medium length; hooked slightly downward; with medium length narrow base. Color—Russet, Plate XV (Ridgway). *Small prickles*—very few. Color—Russet, Plate XV (Ridgway). *Hairs*—none.

Growth—Continued.

*Branches*:—Color—Light Elm Green, Plate XVII (Ridgway) influenced by whitish bloom. *Large prickles*—several; medium length; hooked slightly downward; with medium length narrow base. Color—Tawny, Plate XV (Ridgway). *Small prickles*—few. Color—Cinnamon-Brown, Plate XV (Ridgway). *Hairs*—none.

*New shoots*.—Color—Biscay Green, Plate XVII (Ridgway) overlaid with Mineral Red, Plate XXVII (Ridgway). *Large prickles*—several; medium length; hooked slightly downward; with medium length narrow base. Color—Pomegranate Purple, Plate XII (Ridgway) overlaid on Uranium Green, Plate 63/2, page 63, except at tip.

Growth—Continued.

*Small prickles*—few. Color—Pomegranate Purple, Plate XII (Ridgway). *Hairs*—none.

I claim:

A new and distinct variety of rose plant, characterized as to novelty by its vigorous habit of growth and production of single flowers to a stem; long and graceful form of bud; well-balanced open bloom; fragrance of the flowers and production of the flowers on long stems; color of the flowers; and relatively large foliage having greater than average resistance to mildew, substantially as shown and described.

HERBERT C. SWIM.

No references cited.